US011655334B2

(12) United States Patent
Janka

(10) Patent No.: US 11,655,334 B2
(45) Date of Patent: *May 23, 2023

(54) OXIDATION PROCESS TO PRODUCE 5 METHYL 5-METHYLFURAN-2-CARBOXYLATE (MMFC)

(71) Applicant: Eastman Chemical Company, Kingsport, TN (US)

(72) Inventor: Mesfin Ejerssa Janka, Kingsport, TN (US)

(73) Assignee: Eastman Chemical Company, Kingsport, TN (US)

( * ) Notice: Subject to any disclaimer, the term of this patent is extended or adjusted under 35 U.S.C. 154(b) by 118 days.

This patent is subject to a terminal disclaimer.

(21) Appl. No.: 16/430,717

(22) Filed: Jun. 4, 2019

(65) Prior Publication Data
US 2019/0390004 A1 Dec. 26, 2019

Related U.S. Application Data

(60) Provisional application No. 62/689,619, filed on Jun. 25, 2018.

(51) Int. Cl.
| C08G 63/676 | (2006.01) |
| B01J 27/128 | (2006.01) |
| C07D 307/68 | (2006.01) |

(52) U.S. Cl.
CPC .......... *C08G 63/676* (2013.01); *B01J 27/128* (2013.01); *C07D 307/68* (2013.01)

(58) Field of Classification Search
None
See application file for complete search history.

(56) References Cited

U.S. PATENT DOCUMENTS

| 3,577,411 A | 5/1971 | Liechti et al. |
| 3,584,039 A | 6/1971 | Meyer |
| 3,996,271 A | 12/1976 | Yokota et al. |
| 4,158,738 A | 6/1979 | Scott et al. |
| 5,095,141 A | 3/1992 | Schammel et al. |
| 8,772,513 B2 | 7/2014 | Janka et al. |
| 8,796,477 B2 | 8/2014 | Janka et al. |
| 8,846,960 B2 | 9/2014 | Janka et al. |
| 8,865,921 B2 | 10/2014 | Munoz de Diego et al. |
| 9,156,805 B2 | 10/2015 | Shaikh et al. |
| 9,206,149 B2 | 12/2015 | Janka et al. |
| 9,765,045 B2 | 9/2017 | Strensrud et al. |
| 10,344,011 B1 | 7/2019 | Parker et al. |
| 10,421,736 B2 | 9/2019 | Fontenot et al. |
| 10,526,301 B1 | 1/2020 | Fontenot et al. |
| 10,544,118 B2 | 1/2020 | Janka et al. |
| 10,882,032 B2 | 1/2021 | Fontenot et al. |
| 10,941,245 B2 | 3/2021 | Janka et al. |
| 2005/0208582 A1 | 9/2005 | Ohi et al. |
| 2006/0205977 A1 | 9/2006 | Sumner, Jr. et al. |
| 2012/0059178 A1 | 3/2012 | Sanborn |
| 2012/0283452 A1 | 11/2012 | Munoz De Diego et al. |
| 2012/0302768 A1 | 11/2012 | Janka et al. |
| 2012/0302769 A1 | 11/2012 | Janka et al. |
| 2012/0302770 A1 | 11/2012 | Janka et al. |
| 2012/0302771 A1 | 11/2012 | Janka et al. |
| 2012/0302772 A1 | 11/2012 | Shaikh et al. |
| 2012/0302773 A1 | 11/2012 | Janka et al. |
| 2013/0345447 A1 | 12/2013 | Shaikh et al. |
| 2013/0345448 A1 | 12/2013 | Shaikh et al. |
| 2014/0066639 A1 | 3/2014 | Janka et al. |
| 2014/0128623 A1 | 5/2014 | Janka et al. |
| 2014/0128624 A1 | 5/2014 | Janka et al. |
| 2015/0315166 A1 | 11/2015 | Stensrud et al. |
| 2016/0024039 A1 | 1/2016 | Mazoyer et al. |
| 2016/0207898 A1 | 7/2016 | Singh et al. |
| 2016/0221980 A1 | 8/2016 | Parker et al. |
| 2017/0313670 A1 | 11/2017 | De Sousa Dias et al. |
| 2018/0155306 A1 | 6/2018 | McKay et al. |
| 2019/0023677 A1 | 1/2019 | Fontenot et al. |
| 2019/0031634 A1 | 1/2019 | Metkar et al. |
| 2019/0389820 A1 | 12/2019 | Janka |
| 2019/0389822 A1 | 12/2019 | Janka |
| 2019/0389823 A1 | 12/2019 | Janka |
| 2019/0389824 A1 | 12/2019 | Janka |
| 2019/0389825 A1 | 12/2019 | Janka |
| 2019/0389846 A1 | 12/2019 | Janka |

(Continued)

FOREIGN PATENT DOCUMENTS

| DE | 1146055 B | 3/1963 |
| EP | 2784069 A1 | 10/2014 |
| WO | WO 2011/043660 A2 | 4/2011 |

(Continued)

OTHER PUBLICATIONS

Shen et al. Facile preparation of bio-based polyesters from furandicarboxylic acid and long chain diols via asymmetric monomer stategy. Green Chem, 2017, 19, 4930 (Year: 2017).*

Moraes, Maria De Lourdes L., et al., "Analysis of impurities in crude and highly-purified terephthalic acid by capillary electrophoresis", Journal of the Brazilian Chemical Society, 2004, vol. 15, No. 3, pp. 400-406.

Notification of Transmittal of The International Search Report and The Written Opinion of the International Searching Authority, or the Declaration; International Application No. PCT/US2019/037427 with a filing date of Jun. 17, 2019.

(Continued)

*Primary Examiner* — Tanisha Diggs

(57) ABSTRACT

Disclosed herein is a very efficient method to make 5-(alkoxycarbonyl)furan-2-carboxylic acids (ACFC) from feedstocks comprised of furoates. When a feedstock comprised of methyl 5-methylfuran-2-carboxylate (MMFC) is used a product comprised of (5-(methoxycarbonyl)furan-2-carboxylic acid (MCFC) is obtained in high yield.

16 Claims, 2 Drawing Sheets

(56) References Cited

U.S. PATENT DOCUMENTS

| | | |
|---|---|---|
| 2019/0390004 A1 | 12/2019 | Janka |
| 2020/0123119 A1 | 4/2020 | Fontenot et al. |

FOREIGN PATENT DOCUMENTS

| | | | |
|---|---|---|---|
| WO | WO 2011/043661 A1 | 4/2011 | |
| WO | WO 2012-161967 A1 | 11/2012 | |
| WO | WO 2016-126975 A1 | 8/2016 | |
| WO | WO 2016-195499 A1 | 12/2016 | |
| WO | WO 2016-202858 A1 | 12/2016 | |
| WO | WO 2017-019441 A1 | 2/2017 | |
| WO | WO 2017/076947 A1 | 5/2017 | |
| WO | WO 2019/170204 A1 | 9/2019 | |
| WO | WO 2021/045927 A1 | 3/2021 | |

OTHER PUBLICATIONS

Gandini, Alessandro, et al.; "The Furan Counterpart of Poly(ethylene terephthalate): An Alternative Material Based on Renewable Resources"; Journal of Polymer Science: Part A: Polymer Chemistry, vol. 47, (2009), pp. 295-298.
Co-pending U.S. Appl. No. 16/430,628, filed Jun. 4, 2019, Janka.
Co-pending U.S. Appl. No. 16/430,687, filed Jun. 4, 2019, Janka.
Co-pending U.S. Appl. No. 16/430,694, filed Jun. 4, 2019, Janka.
Co-pending U.S. Appl. No. 16/430,607, filed Jun. 4, 2019, Janka.
Co-pending U.S. Appl. No. 16/430,704, filed Jun. 4, 2019, Janka.
Co-pending U.S. Appl. No. 16/561,469, filed Sep. 5, 2019, Janka.
Co-pending U.S. Appl. No. 16/561,484, filed Sep. 5, 2019, Janka.
Notice of Allowance dated Nov. 20, 2019 received in co-pending U.S. Appl. No. 16/430,607.
USPTO Office Action dated Apr. 10, 2020 received in co-pending U.S. Appl. No. 16/561,469.
USPTO Office Action dated Mar. 6, 2020 received in co-pending U.S. Appl. No. 16/430,704.
USPTO Office Action dated Mar. 9, 2020 received in co-pending U.S. Appl. No. 16/430,687.
USPTO Office Action dated Apr. 14, 2020 received in co-pending U.S. Appl. No. 16/561,484.
USPTO Office Action dated May 18, 2020 received in co-pending U.S. Appl. No. 16/430,694.
Langolf, Sebastian, et al.; Development of Antitrypanosomal and Antiplasmodial Nonpeptidic Cysteine Inhibitors based on N-Protected-Guanidino-Furan and -Pyrrole Building Blocks; ChemMedChem, 2011, 6, pp. 1581-1586.
Schmuck, Carsten, et al.; 2-(Guanidiniocarbonyl)furans as a New Class of Potential Anion Hosts: Synthesis and First Binding Studies; European Journal of Organic Chemistry, 2006, 19, pp. 4385-4392.
Zuo, Xiaobin, et al.; Optimization of Co/Mn/Br-Catalyzed Oxidation of 5-Hydroxymethylfurfural to Enhance 2,5-Furandicarboxylic Acid Yield and Minimize Substrate Burning; ACS Sustainable Chem. Eng., 2016, vol. 4, pp. 3659-3668.
USPTO Office Action dated Jun. 11, 2020 received in co-pending U.S. Appl. No. 16/430,628.
USPTO Office Action dated Jul. 13, 2020 received in co-pending U.S. Appl. No. 16/430,704.
USPTO Office Action dated Sep. 8, 2020 received in co-pending U.S. Appl. No. 16/430,694.
USPTO Office Action dated Oct. 9, 2020 received in co-pending U.S. Appl. No. 16/561,484.
Partenheimer, Walt, et al.; "Synthesis of 2,5-Diformylfuran and Furan-2,5-Dicarboxylic Acid by Catalytic Air-Oxidation of 5-Hydroxymethylfurfural. Unexpectedly Selective Aerobic Oxidation of Benzyl Alcohol to Benzaldehyde with Metal/Bromide Catalysts"; Advanced Synthetic Catal., 2001, 343, No. 1, 102-111.
USPTO Office Action dated Oct. 21, 2020 received in co-pending U.S. Appl. No. 16/430,687.
USPTO Office Action dated Nov. 13, 2020 received in co-pending U.S. Appl. No. 16/430,704.
USPTO Office Action dated Jan. 22, 2021 received in co-pending U.S. Appl. No. 16/561,469.
USPTO Office Action dated Mar. 18, 2021 received in co-pending U.S. Appl. No. 16/430,694.
USPTO Office Action dated Mar. 19, 2021 received in co-pending U.S. Appl. No. 16/430,704.
USPTO Office Action dated Apr. 16, 2021 received in co-pending U.S. Appl. No. 16/561,484.
USPTO Office Action dated May 3, 2021 received in co-pending U.S. Appl. No. 16/460,687.
USPTO Office Action dated Jul. 22, 2021 received in co-pending U.S. Appl. No. 16/430,694.
USPTO Office Action dated Jul. 28, 2021 received in co-pending U.S. Appl. No. 16/430,704.
Tojo, Gabriel et al.; "Oxidation of Primary Alcohols to Carboxylic Acids", Chapter 1, Springer, 2007, 17 pages.
USPTO Notice of Allowance dated Dec. 10, 2020 received in co-pending U.S. Appl. No. 16/430,628.
USPTO Office Action dated Sep. 28, 2021 received in co-pending U.S. Appl. No. 16/561,469.
UPSTO Office Action dated Dec. 9, 2021 received in co-pending U.S. Appl. No. 16/430,694.
USPTO Notice of Allowance dated May 4, 2022 received in co-pending U.S. Appl. No. 16/430,694.
Notification of Transmittal of The International Search Report and The Written Opinion of the International Searching Authority, or the Declaration; International Application No. PCT/US2020/047716 with a filing date of Dec. 4, 2020.
Deng, Jin et al.; Aerobic Oxidation of Hydroxymethylfurfural and Furfural by Using Heterogeneous $Co_xO_y$—N@C Catalysts; Chemsuschem, 2014, 7, pp. 3334-3340.
Co-pending application U.S. Appl. No. 17/753,399, filed Mar. 2, 2022, Janka.

\* cited by examiner

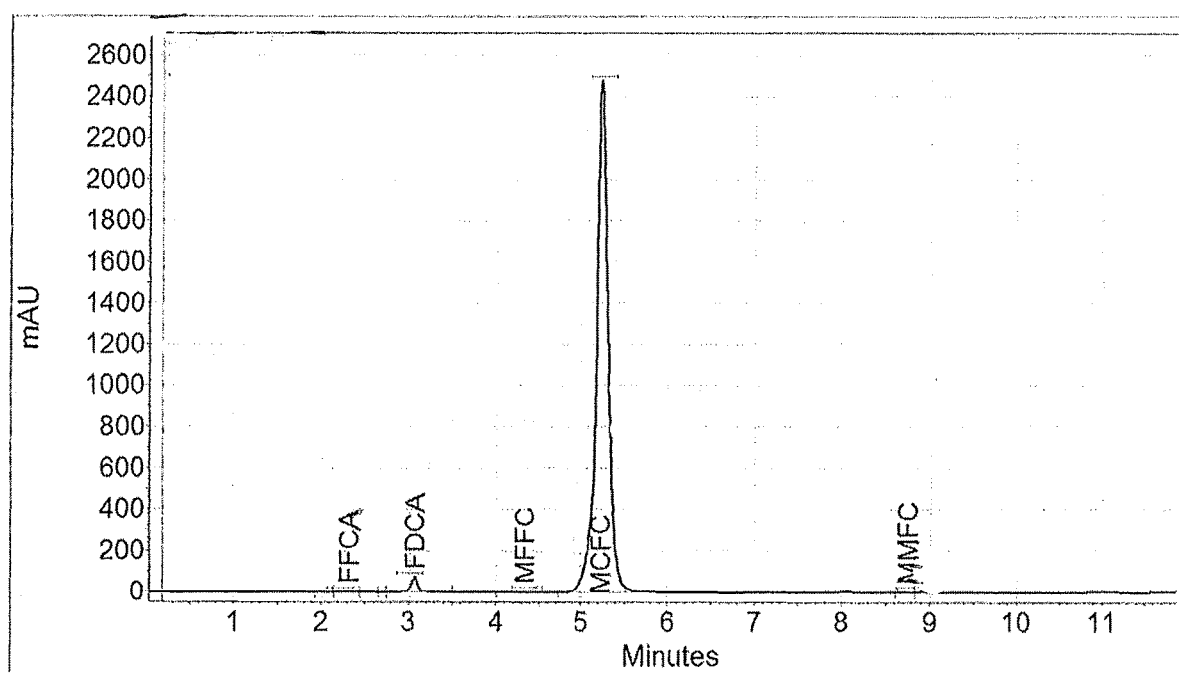
Figure 2. LC chromatogram of white solid product (example 3) isolated from oxidation process.

OXIDATION PROCESS TO PRODUCE 5 METHYL 5-METHYLFURAN-2-CARBOXYLATE (MMFC)

CROSS REFERENCE TO RELATED APPLICATIONS

This application claims priority to U.S. Provisional Application Ser. No. 62/689,619 filed Jun. 25, 2018, now pending, the disclosure of which is herein incorporated by reference in its entirety.

FIELD OF THE INVENTION

The present invention relates to a process to produce a carboxylic acid composition. The process comprises oxidizing at least one oxidizable compound in an oxidizable raw material stream in the presence of an oxidizing gas stream, solvent stream, and at least one catalyst system. Disclosed herein is a very efficient method to make 5-(alkoxycarbonyl) furan-2-carboxylic acids (ACFC) from feedstocks comprised of furoates.

More particularly, when a feedstock comprised of methyl 5-methylfuran-2-carboxylate (MMFC) is used, the present invention relates to a process to produce a carboxylic acid composition comprising 5-(methoxycarbonyl) furan-2-carboxylic acid (MCFC) and compositions thereof. The process comprises oxidizing furates in the presence of oxygen, a saturated organic acid solvent having from 2-6 carbon atoms, and a catalyst system at a temperature of 50° C. to 220° C. to produce the carboxylic acid composition comprising MCFC.

BACKGROUND OF THE INVENTION

Aromatic dicarboxylic acids, such as terephthalic acid and isophthalic acid, are used to produce a variety of polyester products. Important examples of which are poly (ethylene terephthalate) and its copolymers. These aromatic dicarboxylic acids are synthesized by the catalytic oxidation of the corresponding dialkyl aromatic compounds which are obtained from fossil fuels, which is disclosed in U.S. Patent Application 2006/0205977 A1, which is herein incorporated by reference to the extent it does not contradict the statements herein.

There is a growing interest in the use of renewable resources as feed stocks for the chemical industry mainly due to the progressive reduction of fossil reserves and their related environmental impacts. Furan-2,5-dicarboxylic acid (FDCA) and ACFC are versatile intermediates considered as a promising closest biobased alternative to terephthalic acid and isophthalic acid. Like aromatic diacids, ACFC and FDCA can be condensed with diols such as ethylene glycol to make polyester resins similar to polyethylene terephthalate (PET) (Gandini, A.; Silvestre, A. J; Neto, C. P.; Sousa, A. F.; Gomes, M. *J. Poly. Sci. A* 2009, 47, 295.). Therefore, there is a need in the chemical industry for an efficient process to produce carboxylic acid compositions, especially ACFC and FDCA. A high yield process (minimum of 70% ACFC yield) to produce a dry, purified product comprising ACFC is provided herein.

BRIEF DESCRIPTION OF THE DRAWINGS

FIG. 2 illustrates different embodiments of the invention wherein air oxidation experiment of methyl 5 methylfuran-2-carboxylate (MMFC, eq 1, using cobalt, manganese and bromine catalysts system mainly formed 5-(methoxycarbonyl) furan-2-carboxylic acid (MCFC) instead of FDCA.

DETAILED DESCRIPTION

Figure 1:
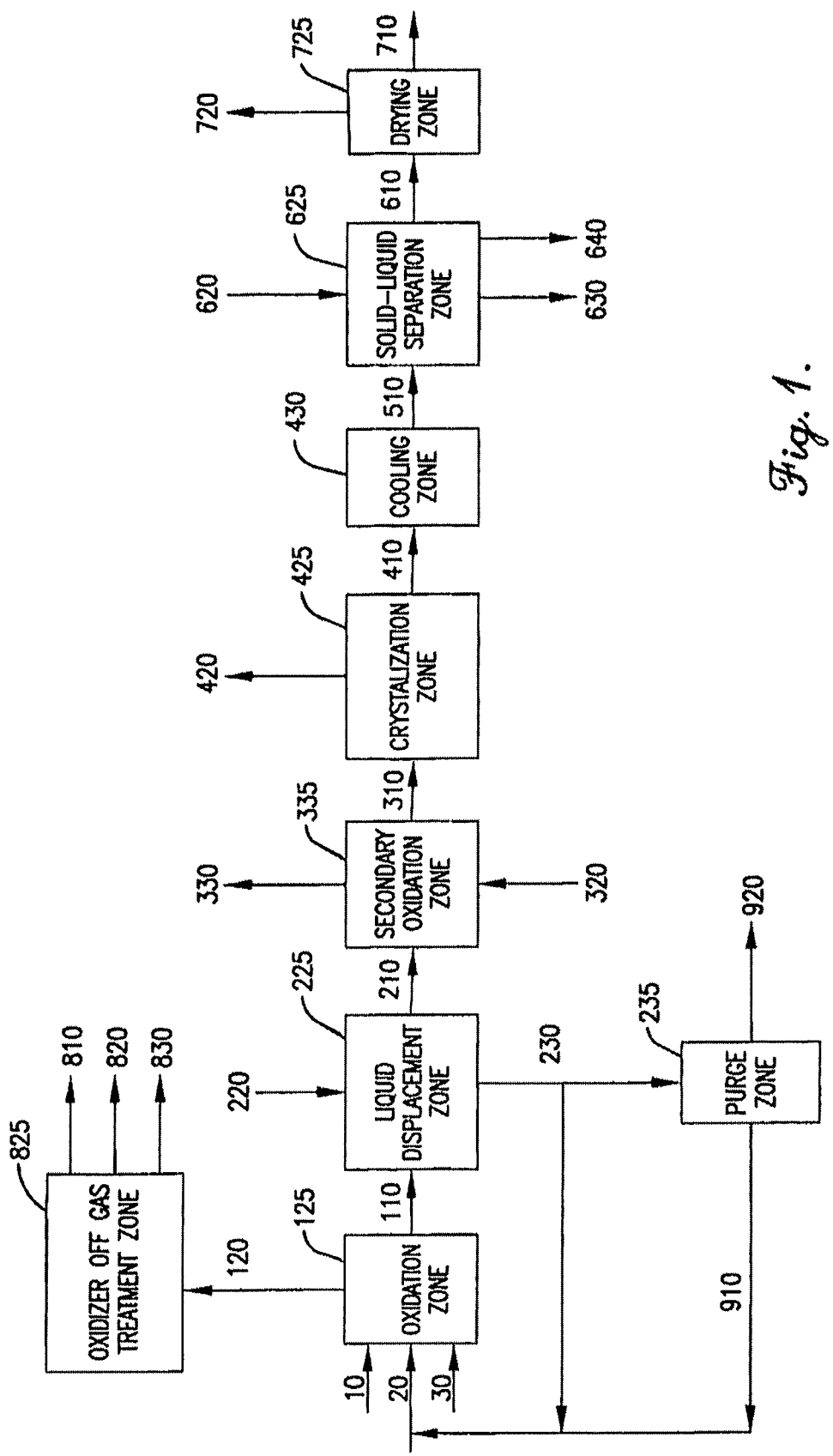
FIG. 1 illustrates different embodiments of the invention to produce a carboxylic acid composition comprising 5-(alkoxycarbonyl)furan-2-carboxylic acids (ACFC).

It should be understood that the following is not intended to be an exclusive list of defined terms. Other definitions may be provided in the foregoing description, such as, for example, when accompanying the use of a defined term in context.

As used herein, the terms "a," "an," and "the" mean one or more.

As used herein, the term "and/or," when used in a list of two or more items, means that any one of the listed items can be employed by itself or any combination of two or more of the listed items can be employed. For example, if a composition is described as containing components A, B, and/or C, the composition can contain A alone; B alone; C alone; A and B in combination; A and C in combination, B and C in combination; or A, B, and C in combination.

As used herein, the terms "comprising," "comprises," and "comprise" are open-ended transition terms used to transition from a subject recited before the term to one or more elements recited after the term, where the element or elements listed after the transition term are not necessarily the only elements that make up the subject.

As used herein, the terms "having," "has," and "have" have the same open-ended meaning as "comprising," "comprises," and "comprise" provided above.

As used herein, the terms "including," "includes," and "include" have the same open-ended meaning as "comprising," "comprises," and "comprise" provided above.

The present description uses numerical ranges to quantify certain parameters relating to the invention. It should be understood that when numerical ranges are provided, such ranges are to be construed as providing literal support for claim limitations that only recite the lower value of the range as well as claim limitations that only recite the upper value of the range. For example, a disclosed numerical range of 10 to 100 provides literal support for a claim reciting "greater than 10" (with no upper bounds) and a claim reciting "less than 100" (with no lower bounds).

The present description uses specific numerical values to quantify certain parameters relating to the invention, where the specific numerical values are not expressly part of a numerical range. It should be understood that each specific numerical value provided herein is to be construed as providing literal support for a broad, intermediate, and narrow range. The broad range associated with each specific numerical value is the numerical value plus and minus 60 percent of the numerical value, rounded to two significant digits. The intermediate range associated with each specific numerical value is the numerical value plus and minus 30 percent of the numerical value, rounded to two significant digits. The narrow range associated with each specific numerical value is the numerical value plus and minus 15 percent of the numerical value, rounded to two significant digits. For example, if the specification describes a specific temperature of 62° F., such a description provides literal support for a broad numerical range of 25° F. to 99° F. (62° F. +/−37° F.), an intermediate numerical range of 43° F. to 81° F. (62° F. +/−19° F.), and a narrow numerical range of 53° F. to 71° F. (62° F. +/−9° F.). These broad, intermediate, and narrow numerical ranges should be applied not only to the specific values, but should also be applied to differences between these specific values. Thus, if the specification describes a first pressure of 110 psia and a second pressure of 48 psia (a difference of 62 psi), the broad, intermediate, and narrow ranges for the pressure difference between these two streams would be 25 to 99 psi, 43 to 81 psi, and 53 to 71 psi, respectively In one embodiment of the invention, a process is provided to produce carboxylic acid composition and/or dry purified carboxylic acid comprising ACFC.

The process comprises oxidizing at least one oxidizable compound in an oxidizable raw material stream 30 in the presence of an oxidizing gas stream 10, solvent stream 20, and at least one catalyst system. The oxidizable raw material stream 30 comprises at least one oxidizable compound suitable to produce a carboxylic acid composition 110 comprising ACFC and FDCA. The amount of ACFC in the carboxylic acid composition 110 can range from greater than 5 by weight percent in the carboxylic acid composition 110, greater than 10 by weight percent in the carboxylic acid composition 110, greater than 20 by weight percent in the carboxylic acid composition 110, greater than 30 by weight percent in the carboxylic acid composition 110, greater than 40 by weight percent in the carboxylic acid composition 110, greater than 50 by weight percent in the carboxylic acid composition 110, greater than 60 by weight percent in the carboxylic acid composition 110, greater than 70 by weight percent in the carboxylic acid composition 110, greater than 80 by weight percent in the carboxylic acid composition 110, greater than 85 by weight percent in the carboxylic acid composition 110, greater than 87 by weight percent in the carboxylic acid composition 110, greater than 90 by weight percent in the carboxylic acid composition 110, greater than 98 by weight percent in the carboxylic acid composition 110. The carboxylic acid composition 110 comprises ACFC, FDCA and solvent.

In another embodiment of the invention, the process comprises oxidizing at least one oxidizable compound in an oxidizable raw material stream 30 in the presence of an oxidizing gas stream 10, solvent stream 20, and at least one catalyst system. The oxidizable raw material stream 30 comprises at least one oxidizable compound selected from the group consisting Methyl 5-methylfuran-2-carboxylate (MMFC), methyl 5-(hydroxymethyl)furan-2-carboxylate, methyl 5-(methoxymethyl)furan-2-carboxylate, methyl 5-(ethoxymethyl)furan-2-carboxylate, ethyl 5-methylfuran-2-carboxylate, ethyl 5-(hydroxymethyl)furan-2-carboxylate, ethyl 5-(methoxymethyl)furan-2-carboxylate, ethyl 5-(ethoxymethyl)furan-2-carboxylate, propyl 5-methylfuran-2-carboxylate, propyl 5-(hydroxymethyl)furan-2-carboxylate, propyl 5-(methoxymethyl)furan-2-carboxylate, propyl 5-(ethoxymethyl)furan-2-carboxylate, isopropyl 5-methylfuran-2-carboxylate, isopropyl 5-(hydroxymethyl)furan-2-carboxylate, isopropyl 5-(methoxymethyl)furan-2-carboxylate, methyl 5-((formyloxy) methyl)furan-2-carboxylate, methyl 5-(acetoxymethyl)furan-2-cayboxylate, methyl 5-((propionyloxy)methyl)furan-2-carboxylate, ethyl 5-((formyloxy) methyl)furan-2-carboxylate, ethyl 5-(acetoxymethyl)furan-2-cayboxylate, ethyl 5-((propionyloxy) methyl)furan-2-carboxylate, propyl 5-((formyloxy) methyl)furan-2-carboxylate, propyl 5-(acetoxymethyl)furan-2-cayboxylate, propyl 5-((propionyloxy)methyl)furan-2-carboxylate, isopropyl 5-((formyloxy)methyl)furan-2-carboxylate, isopropyl 5-(acetoxymethyl)furan-2-cayboxylate, isopropyl 5-((propionyloxy)methyl)furan-2-carboxylate and isopropyl 5-(ethoxymethyl)furan-2-carboxylate to generate a carboxylic acid composition comprising ACFC.

Step (a) comprises oxidizing at least one oxidizable compound in an oxidizable raw material stream 30 in the presence of an oxidizing gas stream 10, solvent stream 20, and at least one catalyst system in a oxidation zone 125 which comprises at least one primary oxidizer reactor to produce a carboxylic acid composition 110 comprising ACFC; wherein the oxidizable raw material stream 30 comprises at least one oxidizable compound selected from the group consisting of Methyl 5-methylfuran-2-carboxylate (MMFC), methyl 5-(hydroxymethyl)furan-2-carboxylate, methyl 5-(methoxymethyl)furan-2-carboxylate, methyl 5-(ethoxymethyl)furan-2-carboxylate, methyl 5-((formyloxy)methyl)furan-2-carboxylate, methyl 5-(acetoxymethyl)furan-2-cayboxylate, and methyl 5-((propionyloxy)methyl)furan-2-carboxylate.

Structures for the various oxidizable raw material compounds are outlined below:

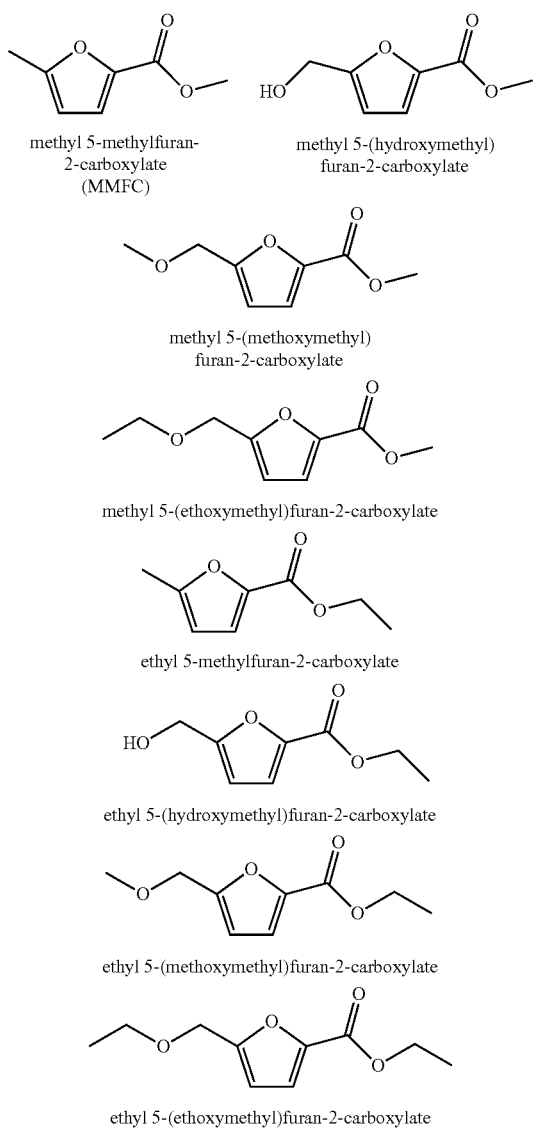

methyl 5-methylfuran-2-carboxylate (MMFC)

methyl 5-(hydroxymethyl)furan-2-carboxylate methyl 5-(methoxymethyl)furan-2-carboxylate methyl 5-(ethoxymethyl)furan-2-carboxylate ethyl 5-methylfuran-2-carboxylate ethyl 5-(hydroxymethyl)furan-2-carboxylate ethyl 5-(methoxymethyl)furan-2-carboxylate ethyl 5-(ethoxymethyl)furan-2-carboxylate

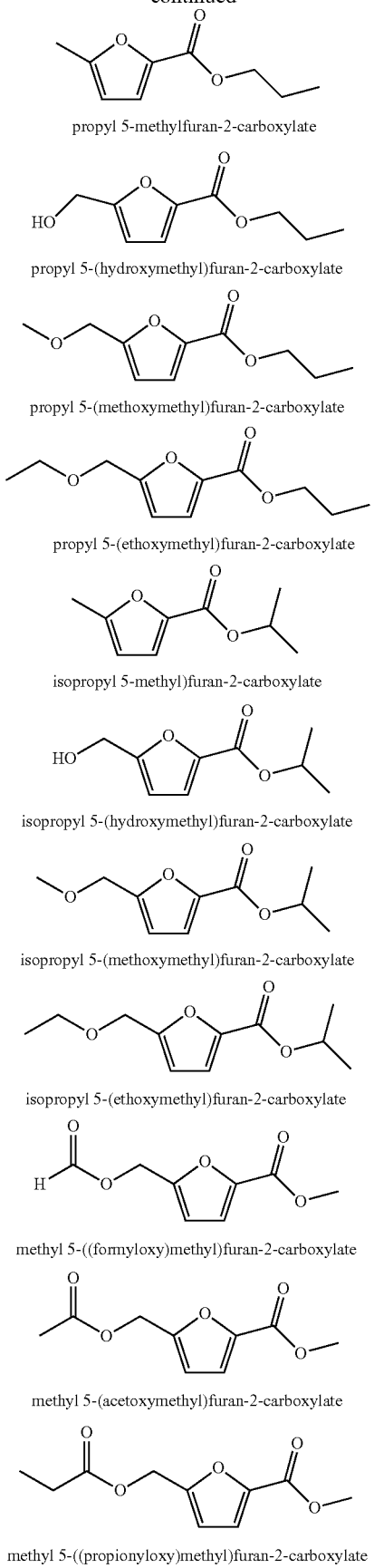
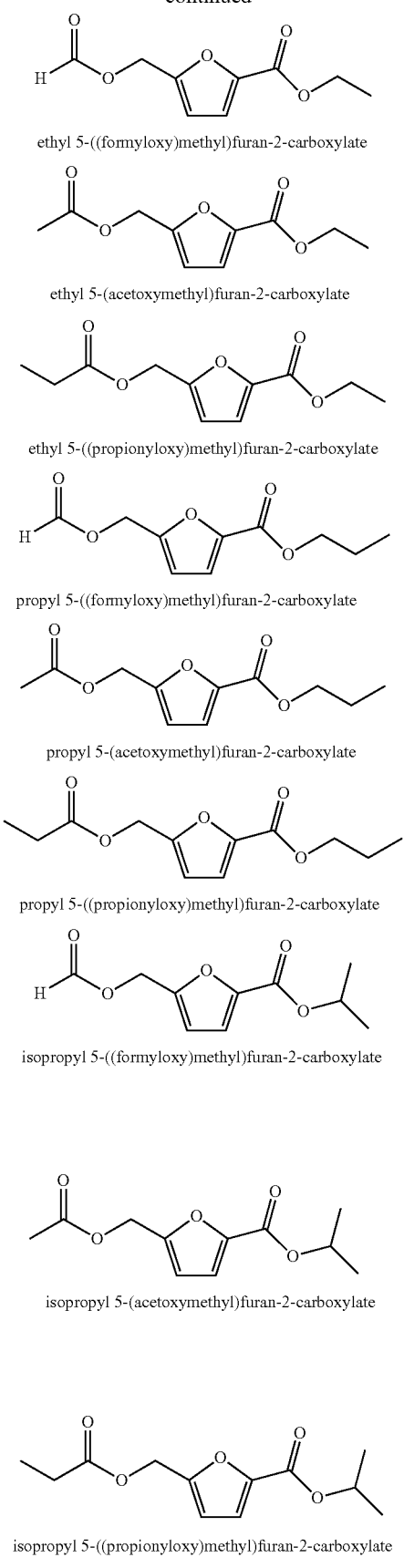

The oxidation of MMFC to MCFC is shown in eq. 1 below.

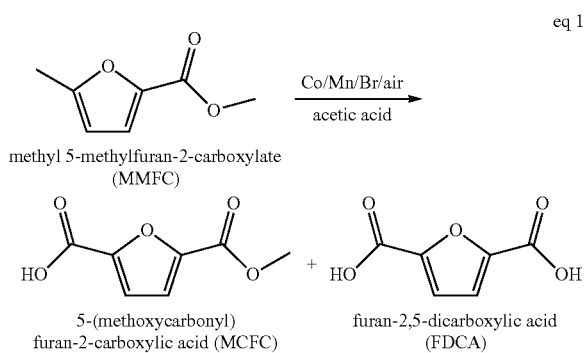

eq 1

In another embodiment of this invention, streams routed to the oxidation zone 125 comprises an oxidizing gas stream 10 comprising oxygen and a solvent stream 20 comprising solvent, an oxidizable raw material stream 30, and a catalyst system. Oxidizable raw material stream 30 comprises a continuous liquid phase. In another embodiment of the invention, the oxidizable raw material stream 30, the oxidizing gas stream 10, the solvent stream 20 and the catalyst system can be fed to the primary oxidization zone 125 as separate and individual streams or combined in any combination prior to entering the oxidation zone 125 wherein said feed streams may enter at a single location or in multiple locations in the oxidization zone 125.

In another embodiment of the invention when a feedstock comprised of methyl 5-methylfuran-2-carboxylate (MMFC) is used said carboxylic acid composition 110 comprises MCFC.

In another embodiment of the invention the carboxylic acid composition 110 comprises FDCA and ACFC In another embodiment, the FDCA in the carboxylic acid composition 110 ranges from 0.01 to 50 wt %, (weight percent), 0.1 wt % to 30 wt % or 0.1 wt % to 0.5 wt %, or 0.1 wt % to 1 wt % or 0.1 wt % to 20 wt % or 0.1 wt % to 10 wt %. In another embodiment of the invention, the MCFC in the carboxylic acid composition 110 comprises at least 5 wt %, at least 10 wt %, at least 15 wt %, at least 20 wt %, at least 30 wt %, at least 40 wt %, at least 50 wt %, at least 60 wt %, at least 70 wt %, at least 80 wt % at least 82 wt % at least 85 wt %, at least 90 wt %, at least 95 wt %, at least 97 wt %, at least 98 wt %, at least 99 wt %.

The catalyst system comprises at least one catalyst suitable for oxidation. Any catalyst known in the art capable of oxidizing the oxidizable compound can be utilized. Example of suitable catalysts comprise at least one selected from, but are not limited to, cobalt, bromine, manganese, zirconium, and nickel compounds, which are soluble in the selected oxidation solvent. In another embodiment of the invention, the catalyst system comprises cobalt, manganese and bromine wherein of cobalt ranges from 2 ppm to 10,000 ppm, manganese ranges from 2 ppm to 10,000 and bromine ranges from 2 ppm to 10,000 ppm in the reaction mixture.

In an embodiment of the invention, the oxidizing gas stream comprises oxygen. Examples include, but are not limited to, air and purified oxygen. The amount of oxygen in the oxidation zone ranges from 5 mole % to 45 mole %, 5 mole % to 60 mole % 5 mole % to 80 mole %.

In an embodiment of the invention, suitable solvents include, but are not limited to, aliphatic mono-carboxylic acids, preferably containing 2 to 6 carbon atoms and mixtures thereof and mixtures of these compounds with water. Examples of aliphatic mono-carboxylic acids, include, but are not limited to acetic acid.

In an embodiment of the invention, suitable solvents include water and the aliphatic solvents. In an embodiment of the invention, the solvents are aliphatic carboxylic acids which include, but are not limited to, aqueous solutions of $C_2$ to $C_6$ monocarboxylic acids, e.g., acetic acid, propionic acid, n-butyric acid, isobutyric acid, n-valeric acid, trimethylacetic acid, caprioic acid, and mixtures thereof. In another embodiment of the invention, the solvent is volatile under the oxidation reaction conditions to allow it to be taken as an off-gas from the oxidation reactor. In yet another embodiment of the invention the solvent selected is also one in which the catalyst composition is soluble under the reaction conditions.

In another embodiment of the invention, the solvent used for the oxidation is an aqueous acetic acid solution, typically having a concentration of 80 wt % to 99 wt %, or 50 wt % to 99 wt %. In yet another embodiment of the invention, the solvent comprises a mixture of water and acetic acid which has a water content of 0% to 15%, 20% by weight. Additionally, a portion of the solvent feed to the primary oxidation reactor may be obtained from a recycle stream obtained by displacing 80 to 90% of the mother liquor taken from the crude reaction mixture stream discharged from the primary oxidation reactor with fresh, wet acetic acid containing 0 to 15%, 20% water.

Suitable solvents include, but are not limited to, aliphatic mono-carboxylic acids, preferably containing 2 to 6 carbon atoms and mixtures thereof and mixtures of these compounds with water. Examples of aliphatic mono-carboxylic acids, include, but are not limited to acetic acid.

Generally, the oxidation temperature can vary from 100° C. to 180° C., or from 110° C. to 180° C., or from 130° C. to 180° C., or from 50° C. to 220° C., from 75° C. to 200° C., from 110° C. to 160° C., from 75° C. to 160° C., and from 130° C. to 160° C.

In another embodiment of the invention, a process is provided to produce ACFC in high yields by liquid phase oxidation that minimizes solvent and starting material loss through carbon burn. The process comprises oxidizing at least one oxidizable compound in an oxidizable raw material stream 30 in the presence of an oxidizing gas stream 10, solvent stream 20, and at least one catalyst system in an oxidation zone 125; wherein the oxidizable compound is at least one selected from the group consisting of Methyl 5-methylfuran-2-carboxylate (MMFC), methyl 5-(hydroxymethyl)furan-2-carboxylate, methyl 5-(methoxymethyl)furan-2-carboxylate, methyl 5-(ethoxymethyl)furan-2-carboxylate, ethyl 5-methylfuran-2-carboxylate, ethyl 5-(hydroxymethyl)furan-2-carboxylate, ethyl 5-(methoxymethyl)furan-2-carboxylate, ethyl 5-(ethoxymethyl)furan-2-carboxylate, propyl 5-methylfuran-2-carboxylate, propyl 5-(hydroxymethyl)furan-2-carboxylate, propyl 5-(methoxymethyl)furan-2-carboxylate, propyl 5-(ethoxymethyl)furan-2-carboxylate, isopropyl 5-methylfuran-2-carboxylate, isopropyl 5-(hydroxymethyl)furan-2-carboxylate, isopropyl 5-(methoxymethyl)furan-2-carboxylate, methyl 5-((formyloxy)methyl)furan-2-carboxylate, methyl 5-(acetoxymethyl)furan-2-cayboxylate, methyl 5-((propionyloxy)methyl)furan-2-carboxylate, ethyl 5-((formyloxy)methyl)furan-2-carboxylate, ethyl 5-(acetoxymethyl)furan-2-cayboxylate, ethyl 5-((propionyloxy)methyl)furan-2-carboxylate, propyl 5-((formyloxy)methyl)furan-2-carboxylate, propyl 5-(acetoxymethyl)furan-2-cayboxylate, propyl 5-((propionyloxy)methyl)furan-2-carboxylate, isopropyl 5-((formyloxy)methyl)furan-2-carboxylate, isopropyl 5-(acetoxymethyl)furan-2-cayboxylate, isopropyl 5-((propionyloxy)methyl)furan-2-carboxylate and isopropyl 5-(ethoxymethyl)furan-2-carboxylate to generate a carboxylic acid composition comprising ACFC.

The oxidizable compound can be oxidized in a solvent comprising acetic acid with or without the presence of water with oxygen in the presence of a catalyst system comprising cobalt, manganese and bromine, such a catalyst system with improved Co:Mn ratio can lead to high yield of ACFC. In this process, the oxidation temperature can vary from 100° C. to 180° C., 110° C. to 180° C., 130° C. to 180° C., 50° C. to 220° C., from 75° C. to 200° C., from 110° C. to 160° C., from 75° C. to 160° C., and from 130° C. to 160° C. which can minimize carbon burn. The cobalt concentration of the catalyst can range from 2 ppm to 10000 ppm, and the amount of manganese from 2 ppm to 10000 ppm, and the amount of bromine from 2 ppm to 10000 ppm with respect to the total weight of the liquid in the reaction medium of the oxidation zone 125. As used herein, process temperature is the temperature of the reaction mixture within the oxidation zone where liquid is present as the continuous phase. The primary oxidizer reactor will typically be characterized by a lower section where gas bubbles are dispersed in a continuous liquid phase. Solids can also be present in the lower section. In the upper section of the primary oxidizer, gas is in the continuous phase and entrained liquid drops can also be present.

In various embodiments of the invention, the catalyst compositions employed in the processes of the invention comprise cobalt atoms, manganese atoms, and bromine atoms, supplied by any suitable means, as further described below. The catalyst composition is typically soluble in the solvent under reaction conditions, or it is soluble in the reactants fed to the oxidation zone. Preferably, the catalyst composition is soluble in the solvent at 25° C., 30° C. or 40° C., and 1 atm, and is soluble in the solvent under the reaction conditions.

The cobalt atoms may be provided in ionic form as inorganic cobalt salts, such as cobalt bromide, cobalt nitrate, or cobalt chloride, or organic cobalt compounds such as cobalt salts of aliphatic or aromatic acids having 2-22 carbon atoms, including cobalt acetate, cobalt octanoate, cobalt benzoate, cobalt acetylacetonate, and cobalt naphthalate.

The oxidation state of cobalt when added as a compound to the reaction mixture is not limited, and includes both the +2 and +3 oxidation states.

The manganese atoms may be provided as one or more inorganic manganese salts, such as manganese borates, manganese halides, manganese nitrates, or organometallic manganese compounds such as the manganese salts of lower aliphatic carboxylic acids, including manganese acetate, and manganese salts of beta-diketonates, including manganese acetylacetonate.

The bromine component may be added as elemental bromine, in combined form, or as an anion. Suitable sources of bromine include hydrobromic acid, sodium bromide, ammonium bromide, potassium bromide, and tetrabromoethane. Hydrobromic acid, or sodium bromide may be preferred bromine sources.

In another embodiment of the invention, in the catalyst system the cobalt to manganese ratio by weight of the catalyst system is at least 0.01:1, 0.1:1, 1:1, 10:1, 20:1, 50:1, 100:1, or 400:1. In another embodiment of the invention the maximum b* content is 0.5, or 1, or 2, or 3, or 4, or 5, or 6, or 7, or 8, or 9, or 10, or 11, or 12, or 13, or 14, or 15, or 16, or 17, or 18, or 19, or 20.

The b* is one of the three-color attributes measured on a spectroscopic reflectance-based instrument. The color can be measured by any device known in the art. A Hunter Ultrascan XE instrument is typically the measuring device. Positive readings signify the degree of yellow (or absorbance of blue), while negative readings signify the degree of blue (or absorbance of yellow).

In another embodiment of the invention, a process is provided for producing ACFC in minimum yields of 80% or 85% or 90% or greater by liquid phase oxidation that minimizes solvent and starting material loss through carbon burn. As used herein, yield is defined as mass of ACFC obtained divided by the theoretical amount of oxidable raw material stream that should be produced based on the amount of raw material use. For example, if one mole or 140.1 grams of MMFC are oxidized, it would theoretically generate one mole or 170.1 grams of MCFC. If for example, the actual amount of MCFC formed is only 150 grams, the yield for this reaction is calculated to be =(150/170.1) times 100, which equals a yield of 88.2%. The same calculation applies for oxidation reaction conducted using other oxidizable compounds.

In another embodiment of this invention, a process is provided comprising oxidizing at least one oxidizable compound in an oxidizable raw material stream 30 in the presence of an oxidizing gas stream 10, solvent stream 20, and at least one catalyst system in a oxidation zone 125; wherein said oxidizable compound is compound selected from the group consisting Methyl 5-methylfuran-2-carboxylate (MMFC), methyl 5-(hydroxymethyl)furan-2-carboxylate, methyl 5-(methoxymethyl)furan-2-carboxylate, methyl 5-(ethoxymethyl)furan-2-carboxylate, ethyl 5-methylfuran-2-carboxylate, ethyl 5-(hydroxymethyl)furan-2-carboxylate, ethyl 5-(methoxymethyl)furan-2-carboxylate, ethyl 5-(ethoxymethyl)furan-2-carboxylate, propyl 5-methylfuran-2-carboxylate, propyl 5-(hydroxymethyl)furan-2-carboxylate, propyl 5-(methoxymethyl)furan-2-carboxylate, propyl 5-(ethoxymethyl)furan-2-carboxylate, isopropyl 5-methylfuran-2-carboxylate, isopropyl 5-(hydroxymethyl)furan-2-carboxylate, isopropyl 5-(methoxymethyl)furan-2-carboxylate, methyl 5-((formyloxy)methyl)furan-2-carboxylate, methyl 5-(acetoxymethyl)furan-2-cayboxylate, methyl 5-((propionyloxy)methyl)furan-2-carboxylate, ethyl 5-((formyloxy)methyl)furan-2-carboxylate, ethyl 5-(acetoxymethyl)furan-2-cayboxylate, ethyl 5-((propionyloxy)methyl)furan-2-carboxylate, propyl 5-((formyloxy)methyl)furan-2-carboxylate, propyl 5-(acetoxymethyl)furan-2-cayboxylate, propyl 5-((propionyloxy)methyl)furan-2-carboxylate, isopropyl 5-((formyloxy)methyl)furan-2-carboxylate, isopropyl 5-(acetoxymethyl)furan-2-cayboxylate, isopropyl 5-((propionyloxy)methyl)furan-2-carboxylate and isopropyl 5-(ethoxymethyl)furan-2-carboxylate to generate a carboxylic acid composition comprising ACFC; wherein said solvent stream comprises acetic acid with or without the presence of water; wherein said catalyst system comprises cobalt, manganese and bromine, wherein the weight ratio of cobalt to manganese in the reaction mixture is from 10 to 400, or 1 to 400, or 10 to 100, or 20 to 100 and the weight ratio of cobalt to bromine is from 0.7 to 3.5, or .5 to 10, or .5 to 5. Such a catalyst system with improved Co:Mn and Co:Br ratio can lead to high yield of ACFC minimum of 60%, 70% , 80%, 85%, 90%, 95%, 98%, 99%, or 99.5%, decrease in the formation of impurities (measured by b*) causing color in the downstream polymerization process while keeping the amount of CO and $CO_2$ in the off-gas at a minimum.

The temperature in the oxidation zone can range from 75° C. to 250° C., and can range from 75° C. to 200° C. or can range from 100° C. to 180° C. or 100° C. to 200° C., or 100° C. to 160° C. One advantage of the disclosed primary oxidation conditions is low carbon burn as illustrated in Table 1. Oxidizer off gas stream 120 is routed to the oxidizer off gas treatment zone 825 to generate an inert gas stream 810, liquid stream 820 comprising water, and a recovered solvent stream 830 comprising condensed solvent. In one embodiment, at least a portion of recovered solvent stream 830 is routed to wash fed stream 620 and the combined stream is routed to the solid-liquid separation zone 625 for the purpose of washing the solids present in the solid-liquid separation zone 625. In one embodiment, the inert gas stream 810 can be vented to the atmosphere. In another embodiment, at least a portion of the inert gas stream 810 can be used as an inert gas in the process for inerting vessels and or used for conveying gas for solids in the process.

In another embodiment of the invention, the composition of the liquid phase within the primary oxidizer can have a pH from −4.0 to 2.0 or the feedstock pH is from −1.8 to 1.0, or the feedstock pH is from −1.5 to 1.0.

It should be understood that steps (b)-(g) are optional and only one possible embodiment of a process to purify the carboxylic acid composition. In addition, in another embodiment of the invention any combination of steps (b) through (g) could be utilized.

Step (b) comprises routing the carboxylic composition 110 and fresh solvent stream 220 to a liquid displacement zone 225 to produce a displaced mother liquor stream 230 and low impurity slurry stream 210 comprising ACFC. The displaced mother liquor stream 230 comprises solvent and soluble matter dissolved in the solvent comprising dissolved impurities and dissolved catalyst. In various embodiments of the invention, from 5% to 99%, from 30% to 90%, and most preferably from 50 to 85% of mother liquor present in the carboxylic acid composition 110 is displaced in the liquid displacement zone 225 resulting in dissolved matter comprising impurities present in the displaced mother liquor not going forward in the process. Sufficient fresh solvent is fed to the liquid displacement zone 225 that becomes mixed with solids present resulting in a low impurity slurry stream 210 being pumpable with weight % solids ranging from 1% to 50%, 10% to 40%, and preferably the weight % solids in stream 210 will range from 25% to 38%.

The liquid displacement zone may be a single unit operation or multiple unit operations. In one embodiment of the invention, the liquid displacement zone 225 may be any solid-liquid separation device capable of generating an isolated wet cake from a feed slurry and then mixing the isolated wet cake with fresh solvent in a separate mixing device to generate the low impurity slurry stream 210. Examples of suitable solid-liquid separation devices include, but are not limited to, a continuous pressure drum filter, solid bowl centrifuges including, but not limited to, decanter and disc stack centrifuges, and batch pressure filters including, but not limited to, candle and leaf filters. The preferred solid-liquid separation device for this application is a continuous pressure drum filter. The solid-liquid separator is operated at temperatures between 30 degrees C. to 200 degrees C., preferably 80 degrees C. to 170. degree. C. The solid-liquid separator in the liquid displacement zone 225 may be operated in continuous or batch mode, although it will be appreciated that for commercial processes, the continuous mode is preferred. Alternatively, a portion of the mother liquor in stream 110 is displaced with fresh liquor stream 220 in a single device to form the low impurity slurry stream 210 without forming an isolated wet cake.

In one embodiment, from 5% to 100% by weight of the displaced mother liquor stream 230 is routed to a purge zone 235 wherein a portion of the impurities present in stream 230 are isolated and exit the process as purge stream 920, wherein a portion is 5% by weight or greater. Recovered solvent stream 910 comprises solvent and catalyst isolated from stream 230 and is recycled to the process. In one embodiment, recovered solvent stream 910 is recycled to the oxidation zone 125 and contains greater than 30% of the catalyst that entered the purge zone 235 in stream 230. In another embodiment, stream 910 is recycled to the oxidation zone 125 and contains greater than 50 weight %, contains greater than 70 weight %, and preferably greater than 90 weight % of the catalyst that enters the purge zone 235 in stream 230 on a continuous or batch basis.

In another embodiment of this invention, a portion up to 100% of the carboxylic acid composition 110 may be routed directly to a secondary oxidation zone 335 without being subjected to the liquid displacement zone 225. In another embodiment of the invention, up to 100% of the feed to the purge zone 235 may be a mother liquor stream 630 generated in a solid-liquid separation zone 625 which also produces the purified wet cake stream 610.

In yet another embodiment, up to 100% of the feed to the purge zone 235 may be mother liquor generated in a secondary liquid displacement zone located at some location downstream of the secondary oxidation zone 335. A secondary liquid displacement zone is not show in FIG. 1, and it comprises equipment like that described for the liquid displacement zone 225 located after the oxidation zone 125, and must be located after the secondary oxidation zone 335.

Step (c) comprises oxidizing the low impurity slurry stream 210 in a secondary oxidation zone 335 to form a purified slurry stream 310. In one embodiment of the invention, the low impurity slurry stream 210 is routed to a secondary oxidation zone 335 where it is heated to between 115 degrees C. and 220 degrees C., and preferably between 120 degrees C. to 200 degrees C. and further oxidized with an oxidizing gas, such as air, fed by line 320 to produce a purified slurry stream 310. The secondary oxidation zone comprises at least one oxidation reactor vessel. In one embodiment, the secondary oxidation zone can be one or more oxidation vessels. When the carboxylic acid in low impurity slurry stream 210 is ACFC, the secondary oxidation zone is operated at a temperature ranging from 115 degrees C. to 220 degrees C., preferably between 120 degrees C. to 200 degrees C., and stream 210 is further oxidized with an oxidizing gas stream fed by line 320 to produce a purified slurry stream 310.

Generally, oxidation in the secondary oxidation zone 335 is at a higher temperature than the oxidation in the oxidation zone 125 to enhance the impurity removal. In one embodiment, the secondary oxidation zone 335 is operated at 30° C., 20° C., and preferably 10° C. higher temperature than the oxidation temperature in the oxidation zone 125 to enhance the impurity removal. The secondary oxidation zone 335 can be heated directly with solvent vapor, or steam via stream 320 or indirectly by any means known in the art.

The amount of oxygen fed in the secondary oxidation zone 335 in controlled to limit the burning of organic molecules to $CO_2$. The amount of oxygen in stream 330 is monitored and used to control the amount of oxygen fed in stream 320. Another function of the secondary oxidation zone 335 is to dissolve and recrystallize solids present in the low impurity slurry stream 210 fed to the secondary oxidation zone. At least 10% by weight, 25% by weight, 50% by weight, and preferably at least 85% by weight of solid impurities and oxidation by-products in stream 210 feed to the secondary oxidation zone 335 go into solution as the ACFC particles are dissolved and re-crystallized in the secondary oxidation zone 335. Off gas from the secondary oxidation zone is withdrawn via line 330 and fed to a recovery system where the solvent is removed from the off gas comprising volatile organic compounds (VOCs). VOCs including methyl bromide may be treated, for example by incineration in a catalytic oxidation unit. The purified slurry stream 310 generated in the secondary oxidation zone is routed to the crystallization zone 425.

Step (d) comprises crystallizing the secondary oxidation slurry 310 in a crystallization zone 425 to form a crystallized slurry stream 410. Generally, the crystallization zone 425 comprises at least one crystallizer. Vapor from the crystallization zone can be condensed in at least one condenser and returned to the crystallization zone 425 or routed away from crystallization zone 425. Optionally, the liquid from the condenser or vapor product from the crystallization zone can be recycled, or it can be withdrawn or sent to an energy recovery device. In addition, the crystallizer off gas is removed via line 420 and can be routed to a recovery system where the solvent is removed, and crystallizer off gas comprising VOCs may be treated, for example, by incineration in a catalytic oxidation unit. When the carboxylic acid is ACFC, the purified slurry stream 310 from the secondary oxidation zone 335 is fed to a crystallization zone 425 comprising at least one crystallizer where it is cooled to a temperature between 40. degrees C. to 175 degrees C. to form a crystallized slurry stream 410, preferably to a temperature between 50 degrees C. to 170 degrees C., and most preferably from 60 degrees C. to 165 degrees C., or 20 to 175 degrees C., 25 to 100 degrees C., 25 to 50 degrees C.

The crystallized slurry stream 410 is then routed to a cooling zone 430 to generate a cooled crystallized slurry stream 510. The cooling of the crystallized slurry stream 410 can be accomplished by any means known in the art. Typically, the cooling zone 430 comprises a flash tank. The temperature of stream 510 can range from 35° C. to 160° C., 45° C. to 120° C., and preferably from 55° C. to 95° C., or 20° C. to 160° C., or 20° C. to 120° C., or 20° C. to 70° C.

In another embodiment, a portion of up to 100% of the secondary oxidation slurry stream 310 is routed directly to the cooling zone 430, thus the portion is not subjected to a crystallization zone 425. In yet another embodiment, a portion of up to 100% of the crystallized slurry stream 410 is routed directly to a secondary liquid displacement zone which is not illustrated in FIG. 1. Up to 100% of the slurry effluent comprising ACFC from a secondary liquid displacement zone can be routed to the solid-liquid separation zone 625 and or routed directly to the cooling zone 430. The function of the secondary liquid displacement zone is to displace a portion of solvent in the crystallized slurry stream 410 with fresh solvent and or water wherein a portion must be greater than 5 weight percent. The secondary liquid displacement zone is separate and distinct from the liquid displacement zone 225 located after the oxidation zone 125. The same type of equipment may be used for both the primary and secondary liquid displacement zones. In yet another embodiment, crystallized slurry stream 410 can be routed directly to the solid-liquid separation zone 625 without being first processed in the cooling zone 430.

Step (e) comprises isolating, washing, and dewatering solids present in the cooled, crystallized slurry stream 510 in the solid-liquid separation zone 625. These functions may be accomplished in a single solid-liquid separation device or multiple solid-liquid separation devices. The solid-liquid separation zone 625 comprises at least one solid-liquid separation device capable of separating solids and liquids, washing solids with a wash solvent stream 620, and reducing the % moisture in the washed solids to less than 30 weight %, less than 25 weight %, less than 20 weight %, less than 15 weight %, and preferably less than 10 weight %.

Equipment suitable for the solid liquid separation zone 625 can typically be comprised of, but not limited to, the following types of devices: centrifuges, cyclones, rotary drum filter, belt filters, pressure leaf filters, candle filters, etc. The preferred solid liquid separation device for the solid liquid separation zone 625 is a rotary pressure drum filter. The temperature of the cooled, crystallized slurry steam 510 which is routed to the solid-liquid separation zone 625 can range from 50° C. to 140° C., or 70° C. to 120° C., and is preferably from 75° C. to 95° C. or 20° C. to 140° C., or 25° C. to 120° C., or 20° C. to 70° C. The wash solvent stream 620 comprises a liquid suitable for displacing and washing mother liquor from the solids.

In one embodiment of the invention, a suitable wash solvent comprises acetic acid and water. In another embodiment, a suitable solvent comprises water up to 100% water. The temperature of the wash solvent can range from 20° C. to 135° C., 40° C. and 110° C., and preferably from 50° C. to 90° C., or 20° C. to 70° C. The amount of wash solvent used is defined as the wash ratio and equals the mass of wash divided by the mass of solids on a batch or continuous basis. The wash ratio can range from 0.3 to 5, 0.4 to 4, and preferably from 0.5 to 3.

After solids are washed in the solid liquid separation zone, they are dewatered. Dewatering involves reducing the mass of moisture present with the solids to less than 30% by weight, less than 25% by weight, less than 20% by weight, less than 15% by weight, and most preferably less than 10% by weight resulting in the generation of a purified wet cake stream 610. In one embodiment, dewatering is accomplished in a filter by passing a gas stream through the solids to displace free liquid after the solids have been washed with a wash solvent. In another embodiment, dewatering is achieved by centrifugal forces in a perforated bowl or solid bowl centrifuge. Stream 630 generated in the solid-liquid separation zone 625 is a mother liquor stream comprising oxidation solvent, catalyst, and some impurities and oxidation byproducts. In one embodiment, a portion of stream 630 is routed to a purge zone 235 and a portion is routed back to the oxidation zone 125 wherein a portion is at least 5 weight %. Wash liquor stream 640 is also generated in the solid-liquid separation zone 625 and comprises a portion of the mother liquor present in stream 510 and wash solvent wherein the ratio of mother liquor mass to wash solvent mass is less than 3 and preferably less than 2.

Step (f) comprises drying the purified wet cake stream 610 in a drying zone 725 to generate a dry purified carboxylic acid 710 and a vapor stream 720. In one embodiment, vapor stream 720 comprises wash solvent vapor. In another embodiment, vapor stream 720 comprises oxidation solvent and wash solvent. The drying zone 725 comprises at least one dryer and can be accomplished by any means known in the art that is capable of evaporating at least 10% of the volatiles remaining in the purified wet cake stream 610 to produce the dried, purified carboxylic acid 710 comprising purified ACFC and a vapor stream 720. For example, indirect contact dryers include, but are not limited to, a rotary steam tube dryer, a Single Shaft Porcupine RIM dryer, and a Bepex Solidaire® dryer. Direct contact dryers include, but are not limited to, a fluid bed dryer and drying in a convey line can be used for drying to produce stream 710. The dried, purified carboxylic acid 710 comprising purified ACFC can be a carboxylic acid composition with less than 8% moisture, preferably less than 5% moisture, and more preferably less than 1% moisture, and even more preferably less than 0.5%, and yet more preferably less than 0.1%. In another embodiment of this invention, if the liquid portion of the purified wet cake stream 610 comprises water and contains less than 0.1 weight % acetic acid, less than 500 ppm wt acetic acid, and preferably less than 200 ppm wt, the stream 610 can be fed directly to a polymerization zone without first being dried.

In one embodiment of the invention, a vacuum system can be utilized to draw vapor stream 720 from the drying zone 725. If a vacuum system is used in this fashion, the pressure of stream 720 at the dryer outlet can range from 760 mmHg to 400 mmHg, from 760 mmHg to 600 mmHg, from 760 mmHg to 700 mmHg, from 760 mmHg to 720 mmHg, and from 760 mmHg to 740 mmHg wherein pressure is measured in mmHg above absolute vacuum. The contents of the conduit between solid-liquid separation zone 625 and drying zone 725 utilized to transfer the purified wet cake stream 610 comprises wet cake stream and gas wherein gas is the continuous phase.

The pressure at the exit of the solid liquid separation zone 625 can be close to that of the pressure where vapor stream 720 exits the drying zone 725, wherein close is defined as within 2 psig, within 0.8 psig, and preferably within 0.4 psig.

In an embodiment of the invention, the dried, purified carboxylic acid 710 has a b* less than 20, or, 15, or 0, or 9.0, or 5, or 4, or 3, or 2, or 1, or 0.5. In another embodiment of the invention, the b* color of the dried, purified carboxylic acid 710 is less than 6.0. In another embodiment of the invention, the b* color of the dried, purified carboxylic acid 710 is less than 5.0. In another embodiment of the invention, the b* color of the dried, purified carboxylic acid 710 is less than 4.0. In another embodiment of the invention, the b* color of the dried, purified carboxylic acid 710 is less than 3.

In an embodiment of the invention, the dried, purified carboxylic acid 710 has less than 1 weight % of FFCA, has less than 0.5 weight % of FFCA, has less than 0.3 weight % of FFCA, has less than 0.1 weight % of FFCA, has less than 500 ppm of FFCA, has less than 400 ppm of FFCA, has less than 400 ppm of FFCA, has less than 300 ppm of FFCA, has less than 200 ppm of FFCA, has less than 100 ppm of FFCA, has less than 10 ppm of FFCA.

In an embodiment of the invention, the dried, purified carboxylic acid 710 has less than 1 weight % of AFFC, has less than 0.5 weight % of AFFC, has less than 0.3 weight % of AFFC, has less than 0.1 weight % of AFFC, has less than 500 ppm of AFFC, has less than 400 ppm of AFFC, has less than 400 ppm of AFFC, has less than 300 ppm of AFFC, has less than 200 ppm of AFFC, has less than 100 ppm of AFFC, has less than 10 ppm of AFFC.

In an embodiment of the invention, the dried, purified carboxylic acid 710 has less than 1 weight % of MFFC, has less than 0.5 weight % of MFFC, has less than 0.3 weight % of MFFC, has less than 0.1 weight % of MFFC, has less than 500 ppm of MFFC, has less than 400 ppm of MFFC, has less than 400 ppm of MFFC, has less than 300 ppm of MFFC, has less than 200 ppm of MFFC, has less than 100 ppm of MFFC, has less than 10 ppm of MFFC.

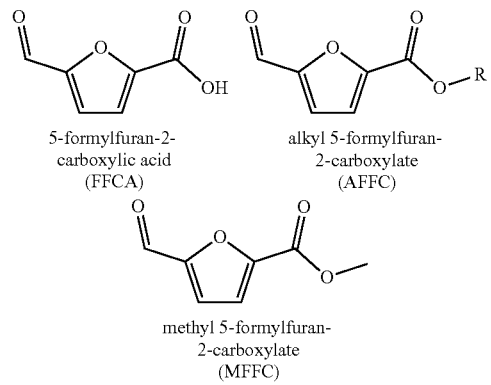

5-formylfuran-2-carboxylic acid (FFCA)

alkyl 5-formylfuran-2-carboxylate (AFFC)

methyl 5-formylfuran-2-carboxylate (MFFC)

It should be appreciated that the process zones previously described can be utilized in any other logical order to produce the dried, purified carboxylic acid 710. It should also be appreciated that when the process zones are reordered that the process conditions may change. It is also understood that all percent values are weight percent.

In another embodiment of the invention the oxidation zone to produce ACFC can comprises at least one oxidizer previously used for a terephthalic acid (TPA) and/or and isophthalic acid (IPA) process. These processes can be any TPA or IPA process known in the art.

An integrated process includes co-locating the two manufacturing facilities, one for oxidation to produce ACFC and for polymerization of the ACFC to produce a composition comprising a polyester, within 10 miles, or within 5 miles, or within 4 miles, or within 3 miles, or within 2 miles, or within 1 mile, or within ½ mile of each other. In an embodiment of the invention, the polyester can comprise PEF (polyethylene furanoate). In another embodiment of the invention, the composition can comprise at least 10% by weight PEF, or comprise at least 20% by weight PEF, or can comprises at least 30% by weight PEF, or can comprises at least 40% by weight PEF. or can comprises at least 50% by weight PEF, or can comprises at least 60% by weight PEF, or can comprises at least 70% by weight PEF, or can comprises at least 80% by weight PEF, or can comprises at least 90% by weight PEF, or can comprises at least 95% by weight PEF, or can comprises at least 98% by weight PEF.

An integrated process also includes having the two manufacturing facilities in solid or fluid communication with each other. If a solid dicarboxylic acid composition is produced, the solids can be conveyed by any suitable means, such as air or belt, to the polymerization facility. If a wet cake dicarboxylic acid composition is produced, the wet cake can be moved by belt or pumped as a liquid slurry to the facility for polymerization.

EXAMPLES

This invention can be further illustrated by the following examples of embodiments thereof, although it will be understood that these examples are included merely for the purpose of illustration and are not intended to limit the scope of the invention unless otherwise specifically indicated.

Oxidation general procedure:

In Examples 1-5, glacial acetic acid (125.7 g) and the catalyst components in the amounts described in Table 1 was transferred to a 300 mL titanium autoclave equipped with a high-pressure condenser, a baffle and an Isco pump. Cobalt, manganese and ionic bromine were provided as cobalt (II)

acetate tetrahydrate, manganese (II) acetate and aqueous hydrobromic acid (48.7 wt. % in water) respectively. The autoclave was pressurized with approximately 50 psig of nitrogen and the homogeneous mixture was heated to the desired temperature in a closed system (i.e., with no gas flow) with stirring. At reaction temperature, an air flow of 1500 sccm was introduced at the bottom of the solution and the reaction pressure was adjusted to the desired pressure. Liquid MMFC was fed at a rate of 0.20 mL/min via a high pressure Isco pump (this is t=0 for the reaction time). After 30 seconds from the start of substrate feeding, 1.0 g of peracetic acid (32 wt. % in acetic acid) in 5.0 g of acetic acid was introduced using a blow-case to start the reaction. The feed was stopped after 1 h and the reaction continued for an additional hour at the same conditions of air flow, temperature and pressure. After the reaction time was completed, the air flow was stopped, and the autoclave was cooled to room temperature and depressurized. The heterogeneous mixture was filtered to isolate a white product. The mass of the filtrate was recorded. The white product was washed with 60 mL of acetic acid two times. The washed white product was oven dried at 110° C. under vacuum overnight and then weighed. The solid product, the filtrate and acetic acid washes were analyzed by Liquid Chromatography.

The Off-gas was analyzed for CO and $CO_2$ by ND-1 R (ABB, Advanced Optima) and $O_2$ by a paramagnetism detection system (Servomex, 1440 Model).

| Time (min) | % A | % B | % C | Flow (ml/min) |
|---|---|---|---|---|
| Initial | 95.0 | 0.0 | 5.0 | 1.50 |
| 6 | 95 | 0 | 5.0 | 1.50 |
| 6.1 | 65 | 30 | 5.0 | 1.50 |
| 9 | 65 | 30 | 5.0 | 1.50 |
| 10.1 | 15 | 80 | 5.0 | 1.50 |
| 12 | 15 | 80 | 5.0 | 1.50 |
| 12.1 | 95 | 0 | 5.0 | 1.50 |
| 17 | 95 | 0 | 5.0 | 1.50 |

EZChrom elite is used for control of the HPLC and for data processing. A 5 point linear calibration was used in the (approximate) range of 0.25 to 100 ppm for FFCA, FDCA, MCFC, MMFC, MFFC. Solid samples were prepared by dissolving ~0.05 g (weighed accurately to 0.0001 g) in 10 ml of 50:50 DMF/THF so ppm level FFCA and MFFC can be detected. For purity analysis, the samples are further diluted by pipetting 100 µL sample into a 10 mL volumetric flask and dilute to volume with 50:50 DMF/THF. Sonication was used to ensure complete dissolution of the sample in the solvent. For liquid samples, 0.1 g of sample is weight out and diluted to 10 mL with 50:50 DMF/THF. A small portion of the prepared sample was transferred to an auto sampler vial for injection onto the LC.

TABLE 1

Results from semi-batch oxidation of MMFC at different conditions.

| Run | Temperature (° C.) | Pressure (psig) | $Co(OAc)_2 4H_2O$ (g) | $Mn(OAc)_2$ (g) | HBr (g)[a] | MMFC (g)[b] | % conversion of MMFC | % yield of MCFC in the solid, in the filtrate and AA washes | % yield of FDCA in the solid, in the filtrate and AA washes |
|---|---|---|---|---|---|---|---|---|---|
| 1 | 110 | 130 | 1.56 | 0.054 | 0.92 | 13.1 | 99.39 | 77.6 | 0.2 |
| 2 | 132 | 130 | 1.56 | 0.060 | 0.93 | 13.1 | 99.94 | 84.7 | 1.7 |
| 3 | 132 | 130 | 1.56 | 1.081 | 0.91 | 13.1 | 99.93 | 77.6 | 1.5 |
| 4 | 155 | 130 | 1.56 | 0.050 | 0.93 | 13.1 | 99.95 | 75.62 | 6.6 |
| 5 | 170 | 130 | 1.57 | 0.050 | 0.92 | 13.1 | 99.98 | 52.5 | 15.2 |

| Run | Solid product composition | | | | b* of the solid | CO (total mol) | CO2 (total mol) | COx (mol/min) |
|---|---|---|---|---|---|---|---|---|
| | MCFC (wt. %) | FDCA (wt. %) | MFFC (ppmw) | FFCA (ppmw) | | | | |
| 1 | 99.39 | 0.036 | 2504.6 | 5.4 | 0.34 | 0.008 | 0.06 | 0.000283 |
| 2 | 98.44 | 1.34 | 95.7 | 1.71 | −0.11 | 0.008 | 0.051 | 0.000246 |
| 3 | 97.56 | 1.15 | 379.8 | 318.6 | 0.62 | 0.011 | 0.008 | 0.000079 |
| 4 | 94.65 | 5.29 | 123.3 | 0 | 0.15 | 0.012 | 0.065 | 0.000321 |
| 5 | 72.63 | 27.26 | 246.6 | 0.002 | −0.59 | 0.01 | 0.107 | 0.000488 |

[a]HBr (48.7 wt. % in water),
[b]MMFC (97.8 wt. %)

Analytical

Liquid chromatographic method for sample analysis: Samples were analyzed with an Agilent 1260 LC unit consisting of a quaternary pump, an autosampler (3 uL injection), a thermostated column compartment (35° C.) and a diode array UV/vis detector (280 nm). The chromatograph was fitted with a 150 mm×4.6 mm Thermo Aquasil C18 column packed with 3 micron particles. The solvent flow program is shown in the table below: Channel A was 0.1% phosphoric acid in water, channel B was acetonitrile, and channel C was tetrahydrofuran (THF).

Color Measurement.

1) Assemble the Carver Press die as instructed in the directions—place the die on the base and place the bottom 40 mm cylinder polished side face-up.

2) Place a 40 mm plastic cup (Chemplex Plasticup, 39.7×6.4 mm) into the die.

3) Fill the cup with the sample to be analyzed. The exact amount of sample added is not important.

4) Place the top 40 mm cylinder polished side face-down on the sample.

5) Insert the plunger into the die. No "tilt" should be exhibited in the assembled die.
6) Place the die into the Carver Press, making sure that it is near the center of the lower platen. Close the safety door.
7) Raise the die until the upper platen makes contact with the plunger. Apply >10,000 lbs. pressure. Then allow the die to remain under pressure for approximately 30 seconds (exact time not critical).
8) Release the pressure and lower the lower platen holding the die.
9) Disassemble the die and remove the cup. Place the cup into a labeled plastic bag (Nasco Whirl-Pak 4 oz).
10) Using a HunterLab UltraScan Pro colorimeter, create the following method (Hunterlab EasyMatchQC software, version 3.6.2 or later)
Mode: RSIN-LAV (Reflectance Specular Included)
Area View: 0.78 in.
UV Filter Position: Nominal
Measurements:
CIE L* a* b*
CIEXYZ
11) Standardize the instrument as prompted by the software using the light trap accessory and the certified white tile accessory pressed against the reflectance port.
12) Run a green tile standard using the certified white tile and compare the CIE X, Y, and Z values obtained against the certified values of the tile. The values obtained should be ±0.15 units on each scale of the stated values.
13) Analyze the sample in the bag by pressing it against the reflectance port and obtaining the spectrum and L*, a*, b* values. Obtain duplicate readings and average the values for the report.

Oxidation of Furoate Based Feedstock:
Air oxidation experiment of methyl 5-methylfuran-2-carboxylate (MMFC, eq 1, using cobalt, manganese and bromine catalysts system mainly formed 5-(methoxycarbonyl) furan-2-carboxylic acid (MCFC) instead of FDCA, FIG. 2. This oxidation reaction produces water as a byproduct but to our surprise (unexpected invention), under certain conditions, hydrolysis of the methyl ester bond by the water to make FDCA was very minimal.

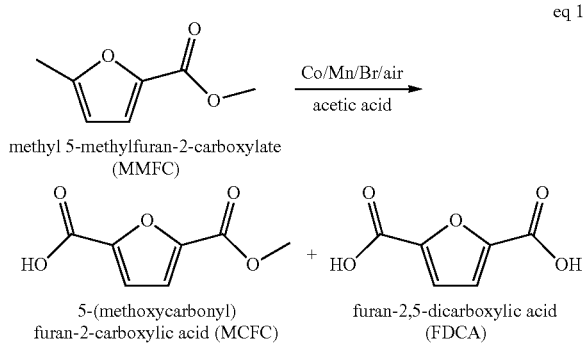

eq 1

Claims not Limited to Disclosed Embodiments

The preferred forms of the invention described above are to be used as illustration only and should not be used in a limiting sense to interpret the scope of the present invention. Modifications to the exemplary embodiments, set forth above, could be readily made by those skilled in the art without departing from the spirit of the present invention.

The inventors hereby state their intent to rely on the Doctrine of Equivalents to determine and assess the reasonably fair scope of the present invention as it pertains to any apparatus not materially departing from but outside the literal scope of the invention as set forth in the following claims.

I claim:

1. A composition comprising the following:
5-(methoxycarbonyl) furan-2-carboxylic acid (MCFC) in an amount greater than 98 wt %; furan-2,5-dicarboxylic acid (FDCA) present in an amount less than 2 wt %; 5 formlyfuran-2-carboxylic acid (FFCA) present in an amount less than 1 wt %; methyl 5-formylfuran-2-carboxylate (MFFC) present in an amount less than 1 wt %; and wherein said composition has a b* less than 5.

2. A composition according to claim 1 wherein FFCA is present in an amount less than 0.5wt %.

3. A composition according to claim 1 wherein MFFC is present in an amount less than 0.5 wt %.

4. A composition according to claim 2 wherein MFFC is present in an amount less than 0.5 wt %.

5. A composition according to claim 1 wherein FFCA is present in an amount less than 0.1 wt %.

6. A composition according to claim 1 wherein MFFC is present in an amount less than 0.1 wt %.

7. A composition according to claim 5 wherein MFFC is present in an amount less than 0.1 wt %.

8. A composition according to claim 1 wherein FFCA is present in an amount less than 500 ppm by weight.

9. A composition according to claim 1 wherein MFFC is present in an amount less than 500 ppm by weight.

10. A composition according to claim 8 wherein MFFC is present in an amount less than 500 ppm.

11. A composition according to claim 1 wherein FFCA is present in an amount less than 100 ppm by weight.

12. A composition according to claim 1 wherein MFFC is present in an amount less than 100 ppm by weight.

13. A composition according to claim 11 wherein MFFC is present in an amount less than 100 ppm by weight.

14. A composition according to claim 1 wherein b* is less than 2.

15. A composition according to claim 1 wherein b* is less than 1.

16. A composition according to claim 1 wherein b* is less than 0.5.

* * * * *